United States Patent
Trantow et al.

(10) Patent No.: US 6,356,069 B1
(45) Date of Patent: Mar. 12, 2002

(54) EDDY CURRENT CALIBRATION STANDARD

(75) Inventors: Richard L. Trantow; Francis H. Little, both of Cincinnati; Gigi O. Gambrell, West Chester; John W. Ertel, New Vienna, all of OH (US)

(73) Assignee: General Electric Company, Cincinnati, OH (US)

( * ) Notice: Subject to any disclaimer, the term of this patent is extended or adjusted under 35 U.S.C. 154(b) by 0 days.

(21) Appl. No.: 09/453,089

(22) Filed: Dec. 2, 1999

Related U.S. Application Data
(60) Provisional application No. 60/155,441, filed on Sep. 23, 1999.

(51) Int. Cl.$^7$ .......................... G01R 35/00; G01B 3/30; G01B 3/14
(52) U.S. Cl. .................. 324/202; 33/1 BB; 33/501.08; 33/551; 33/552; 33/567
(58) Field of Search .......................... 33/1 BB, 501.05, 33/501.08, 549, 551, 552, 567, 567.1, 502; 324/202; 73/601

(56) References Cited

U.S. PATENT DOCUMENTS

| | | | | |
|---|---|---|---|---|
| 1,306,254 A | * | 1/1919 | Deck .......................... 33/567 |
| 2,580,412 A | * | 1/1952 | Darmody ................... 33/555.2 |
| 3,718,855 A | * | 2/1973 | Rogel et al. .............. 324/34 R |
| 4,196,048 A | | 4/1980 | Qurnell et al. ............ 294/86 A |
| 4,771,549 A | * | 9/1988 | Shelangoskie et al. ....... 33/563 |
| 5,193,286 A | * | 3/1993 | Collier ........................ 33/552 |
| 5,315,234 A | | 5/1994 | Sutton, Jr. et al. .......... 324/242 |
| 5,329,230 A | | 7/1994 | Viertl et al. ................. 324/262 |
| 5,329,703 A | * | 7/1994 | Graig .......................... 33/567 |
| 5,345,514 A | | 9/1994 | Mahdavieh et al. ............ 382/8 |
| 5,371,462 A | | 12/1994 | Hedengren et al. ......... 324/225 |
| 5,442,286 A | | 8/1995 | Sutton, Jr. et al. .......... 324/242 |
| 5,510,709 A | | 4/1996 | Hurley et al. ............... 324/242 |
| 5,659,248 A | | 8/1997 | Hedengren et al. ......... 324/242 |
| 5,710,378 A | | 1/1998 | Dykes et al. ................. 73/601 |
| 5,903,147 A | | 5/1999 | Granger, Jr. et al. ........ 324/219 |
| 5,931,208 A | * | 8/1999 | Gifkins ...................... 33/567.1 |

FOREIGN PATENT DOCUMENTS
WO    WO 87/00288    * 6/1986

* cited by examiner

Primary Examiner—Diego Gutierrez
(74) Attorney, Agent, or Firm—Andrew C. Hess; V. Ramaswamy

(57) ABSTRACT

A calibration standard for calibrating an eddy current inspection probe sized and shaped to inspect a preselected non-planar feature of a manufactured part. The feature extends in a longitudinal direction and in a lateral direction. Further, the feature has an end profile as viewed in the longitudinal direction having a substantially invariant shape and orientation. The calibration standard includes a body having a non-planar surface extending in a longitudinal direction and in a lateral direction. The standard also has an end profile as viewed in the longitudinal direction of the surface substantially identical to the profile of the feature. The surface of the body has an elongate narrow opening extending into the body substantially normal to the surface and traversing the surface of the body at a substantially constant angle with respect to the longitudinal direction of the surface as viewed normal to the surface.

5 Claims, 2 Drawing Sheets

EDDY CURRENT CALIBRATION STANDARD

This application claims benefit of Provisional Patent Application No. 60/155,441, filed Sep. 23, 1999, which is hereby incorporated by reference.

BACKGROUND OF THE INVENTION

The present invention relates generally to calibration standards, and more particularly, to a standard used to calibrate an eddy current inspection probe.

Eddy current probes are commonly used to detect flaws in surfaces of manufactured parts such as gas turbine engine components. During this type of inspection, electromagnetic induction is used to induce eddy currents in the part being inspected. One or more drive coils inside the probe generate alternating magnetic fields which induce the eddy currents in the part when the probe is moved close to the part. When flaws are present in the part, the flow of eddy currents is altered. The altered eddy currents produce changes in a secondary magnetic field which are detected by the drive coil(s) or by separate sense coils inside the eddy current probe. These coils generate an electrical signal in response to the altered secondary magnetic field. The amplitude of electrical signal is generally proportionate to the size of the flaw within the range of flaw sizes for which the probe is designed. Thus, the size and location of flaws may be detected using eddy current probes.

One type of eddy current probe used for inspecting part features having complex shapes includes an array of drive coils and sensing coils for simultaneously inspecting various portions of the feature. By simultaneously inspecting all portions of the feature, the need to pass the probe over the feature more than once is eliminated. Because only one pass is required, this type of probe has the advantage of reducing inspection time.

Eddy current probes and the associated electronic devices must be calibrated to normalize the response of the coils in the array and to establish the system gain so the amplitude of the response can be correlated to particular flaw sizes. In the past, calibration standards having the specific part geometry have been used to normalize the response of the coils and a separate flat plate having a manufactured flaw of a known size has been used to independently establish system gain. However, this multi-step calibration process takes time. Attempts to make a single pass calibration standard have resulted in large variations in calibration. Because the eddy current inspection results are used to determine the length of service remaining in the inspected part, large variations in calibration result in underestimated part life prediction and premature part retirement which decrease acceptable service intervals and increase maintenance cost.

SUMMARY OF THE INVENTION

Briefly, apparatus of this invention is a calibration standard for calibrating an eddy current inspection probe sized and shaped to inspect a preselected non-planar feature of a manufactured part. The feature extends in a longitudinal direction and in a lateral direction. Further, the feature has an end profile as viewed in the longitudinal direction having a substantially invariant shape and orientation. The calibration standard includes a body having a non-planar surface extending in a longitudinal direction and in a lateral direction. The standard also has an end profile as viewed in the longitudinal direction of the surface substantially identical to the profile of the feature. The surface of the body has an elongate narrow opening extending into the body substantially normal to the surface and traversing the surface of the body at a substantially constant angle with respect to the longitudinal direction of the surface as viewed normal to the surface.

In another aspect, the invention includes a method of manufacturing a calibration standard including forming first and second pieces of a body so each of the pieces has a surface extending in a longitudinal direction and a lateral direction, so each piece has a profile in the longitudinal direction of the respective surface generally similar to the profile of the feature, and so the first and second pieces have mating faces. The method also includes positioning the face of the first piece of the body adjacent the face of the second piece of the body and aligning the surface of the first piece of the body with the surface of the second piece of the body. In addition, the method includes simultaneously machining the surfaces of the first and second pieces of the body after the faces are positioned adjacent each other and the surfaces are aligned to ensure the profiles in the longitudinal directions of the first and second pieces are substantially identical to the profile of the feature and to remove any discontinuities in the surfaces adjacent the faces thereby to eliminate variations in eddy current inspection probe signal during calibration resulting from discontinuities in the surfaces.

In yet another aspect of the present invention, the method includes forming first and second pieces of a body, applying a voltage potential to the first piece of the body relative to the second piece of the body. The method also includes submersing the first and second pieces in an oil and positioning the face of the first piece of the body adjacent the face of the second piece of the body. Further, the method includes moving at least one of the first and second pieces of the body toward the other of the pieces so at least portions of the faces contact each other to simultaneously machine the faces of the pieces by electrical discharge machining.

Other features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENT

Figure 1:
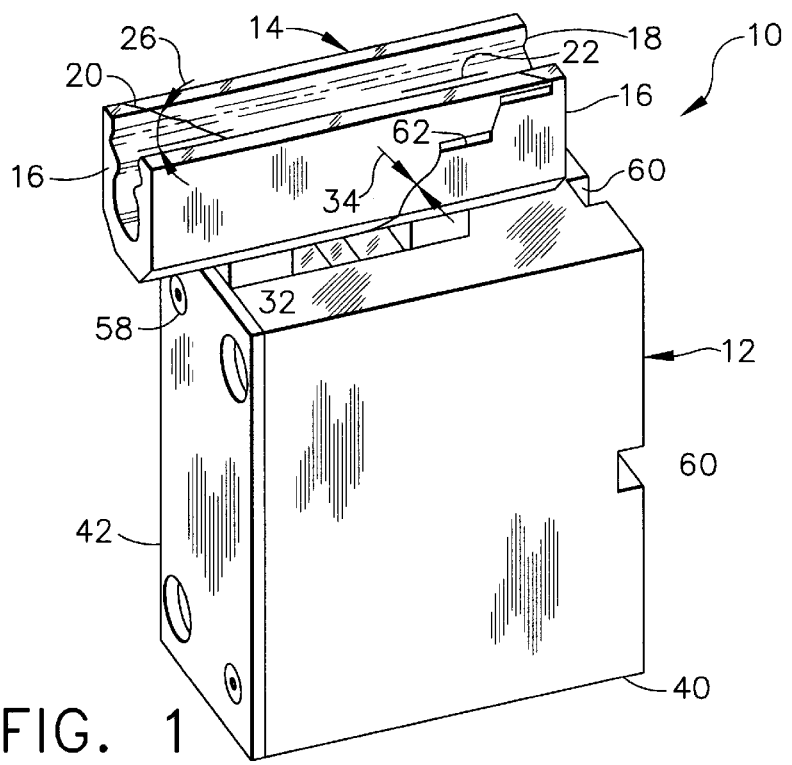
FIG. 1 is a perspective of a calibration standard of the present invention.

Referring now to the drawings and in particular to FIG. 1, a calibration standard of the present invention is designated in its entirety by the reference numeral 10. The standard 10 generally comprises a fixture, generally designated 12, and a body, generally designated 14. The body 14 is formed by two identical pieces 16 which are positioned adjacent each other to form a surface 18 having a narrow elongate crack-simulating opening 20 therein (commonly referred to in the trade as a "notch".

Figure 2:
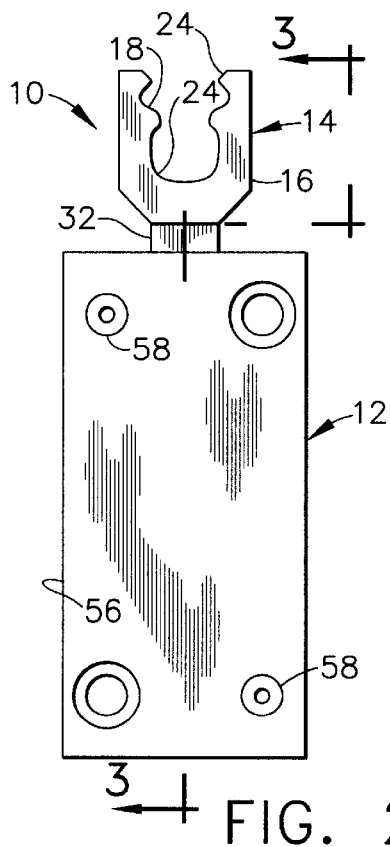
FIG. 2 is a front elevation of the standard.

The surface 18 extends in a longitudinal direction 22 (FIG. 1) and a lateral or transverse direction 24 (FIG. 2). Because the surface 18 is non-planar, the lateral direction 24 varies at different points along the surface. As further illustrated in FIG. 2, the profile of the surface 18 as viewed in the longitudinal direction 22 has a substantially invariant shape and orientation. This shape is substantially identical to a shape of the feature of the machined part for which the standard and corresponding eddy current probe (not shown) are made. For instance, the standard 10 may have a dovetail shape as shown for calibrating a probe used to inspect gas turbine disk dovetails. As those skilled in the art will appreciate, the standard may have other shapes such as a gear tooth profile without departing from the scope of the present invention.

The opening 20 extends into the body 14 substantially normal to the surface 18 and along the surface of the body at a substantially constant angle 26 with respect to the longitudinal direction 22 of the surface as viewed normal to the surface. Thus, when viewed from the side as in FIG. 3, the opening 20 appears to be non-linear. However, if a tracing of the surface 18 was made and flattened out as shown in FIG. 4, the tracing would show the opening 20 forms a straight line extending at the constant angle 26 with respect to the longitudinal direction 22 of the surface. This angle 26 is preferably selected to maximize the signal produced by the probe sense coils. Although other angles may be used without departing from the scope of the present invention, in the preferred embodiment the angle 26 is between about 45 degrees and about 55 degrees. More preferably, the angle 26 is about 50 degrees. Regardless of the specific angle used, the angle 26 is preferably constant along the entire length of the opening 20. In the most preferred embodiment, the angle 26 varies by no more than about one degree along the entire length of the opening 20. As further illustrated in FIG. 1, the opening 20 extends entirely through the body 14 so the body is made in two pieces 16 having mating faces 30 (FIG. 5) which define the opening.

Figure 3:
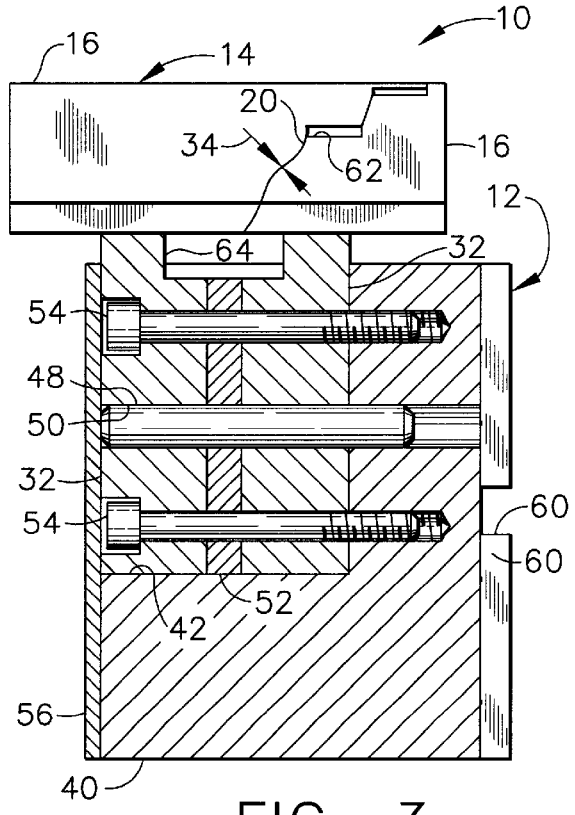
FIG. 3 is a cross section of the standard taken in the planes of line 3—3 of FIG. 2.
Figure 4:
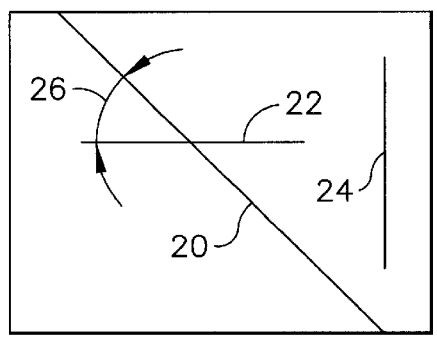
FIG. 4 is a flattened view of a tracing of a surface of the standard having a narrow opening.

As illustrated in FIG. 3, stems 32 extend downward from each of the pieces 16. The fixture 12 is configured to hold these stems 32 so the mating faces 30 of the pieces 16 are spaced by a constant distance (e.g., 0.003 inches) and the opening 20 has a constant width 34 along its entire length. Regardless of the specific width used, the width 34 is preferably constant along the entire length of the opening 20. In the most preferred embodiment, the width 34 varies by less than about 0.001 inches along the entire length of the opening 20. The fixture 12 includes a housing 40 having a slot 42 sized and shaped for holding the stems 32. The machining tolerances of the slot 42 and the stems 32 are tightly controlled to ensure the pieces 16 are precisely positioned in the fixture 12 so the position of the surface 18 and the width of the opening 20 are controlled. A dowel pin 48 extends from the housing 40 into the slot 42 and engages holes 50 provided in the stems 32 to further ensure proper positioning of the pieces 16. A shim 52 provided between the stems maintains the desired slot width 34 between the mating faces 30. Fasteners 54 hold the stems 32 in the slot 42. A cover plate 56 is mounted on the housing 40 with screw fasteners 58 at one end of the slot 42 to cover the stems 32, the dowel pin 48, and the fasteners 54 holding the pieces 16 of the body 14 in the fixture 12. Grooves 60 formed in the housing 40 opposite the cover plate 56 precisely locate the fixture 12 in the eddy current probe calibration fixture (not shown).

Figure 5:
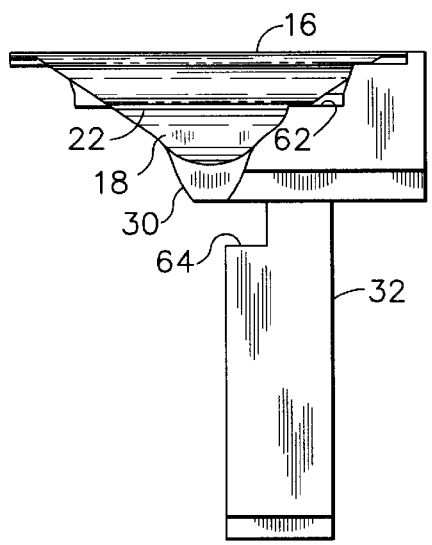
FIG. 5 is a right side elevation of a piece of the standard.
Figure 6:
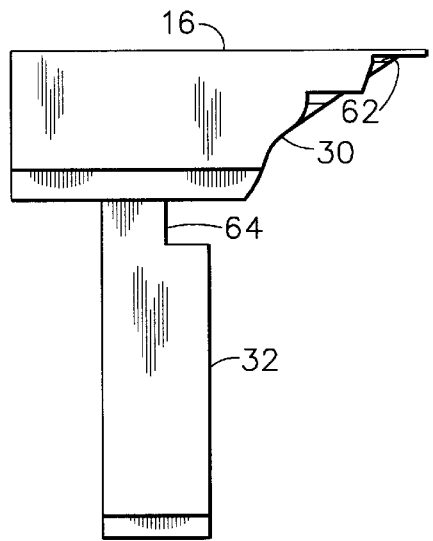
FIG. 6 is a left side elevation of the piece shown in FIG. 5.

The previously described calibration standard 10 is made by machining the pieces 16 of the body 14 to the general configuration shown in FIGS. 5 and 6. Although the pieces may have other shapes without departing from the scope of the present invention, the pieces 16 of the preferred embodiment have shapes identical to each another. The surface 18 of each of the pieces 16 is rough machined so it has a profile in the longitudinal direction 22 generally similar to the profile of the feature of the machined part for which the standard 10 is made. However, some machining stock is left on the surfaces to allow for subsequent machining as will be explained below.

Once the pieces 16 are rough machined, the mating faces 30 of the pieces are milled using a conventional end mill such as a programmable multi-axis end mill (not shown) so the faces extend normal to the surface 18 and at a substantially constant angle 26 (e.g., about 50 degrees) with respect to the longitudinal direction 22. Openings 62 are machined partially through the pieces 16 to provide relief as needed for the end mill collet (not shown). Similarly, slots 64 are formed in the stems 32 as needed for providing relief for the collet.

Figure 7:
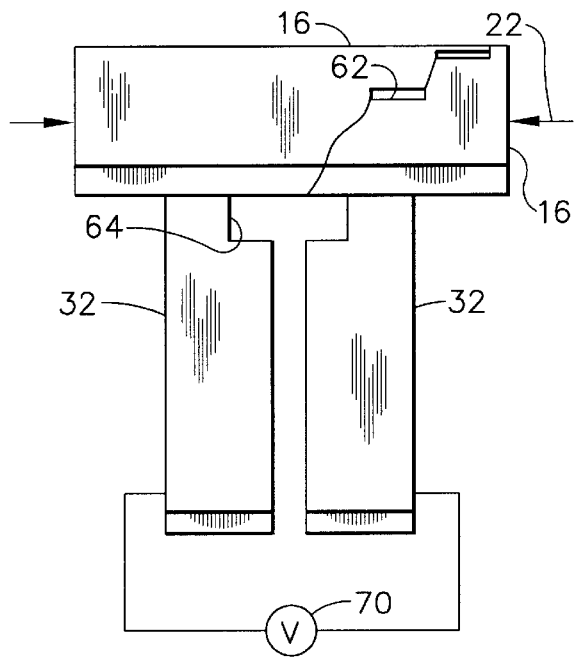
FIG. 7 is a schematic of a final machining operation used to make matched pieces.

The rough machined and milled pieces 16 are positioned so their respective faces 30 are adjacent one another and their respective surfaces 18 are aligned as illustrated in FIG. 7. Once the pieces 16 are so positioned and aligned, the surfaces 18 of the pieces are simultaneously machined using a conventional wire electrical discharge machining (EDM) process to ensure the profiles in the longitudinal directions 22 of the pieces are substantially identical to each other and to the profile of the part feature and to remove any discontinuities in the surfaces adjacent the faces 30. Because surface discontinuities contribute to signal variation during eddy current probe calibration, reducing the surface discontinuities improves the system calibration. Due to process limitations inherent with end milling, small scallops (not shown) are formed in the faces 30 during the end milling operation described above. Once the surfaces 18 are finish machined by the wire EDM process to remove discontinuities, the mating faces 30 are machined to remove the scallops and thereby to ensure the opening 20 has a constant width 34. As schematically illustrated in FIG. 7, the faces 30 are machined by a electrical discharge machining process in which each piece 16 of the body 14 is used as an electrode or cathode to machine the other piece of the body. A voltage potential 70 is applied to one of the pieces 16 of the body 14 relative to the other piece of the body. The pieces 16 are submersed in a conventional EDM oil and at least one of the pieces is moved toward the other piece in the longitudinal direction 22 so at least portions of the faces 30 contact each other to simultaneously machine the faces of the pieces so they exactly match. As will be appreciated by those skilled in the art, removing the scallops left by the end milling process eliminates variations in opening width 34. Because opening width variations contribute to signal variation during eddy current probe calibration, reducing variation in the width 34 improves the system calibration.

Once the pieces 16 are machined, they are positioned in the fixture 12 as previously described. To use the calibration standard 10, an eddy current inspection probe (not shown) sized and shaped to inspect a preselected non-planar feature of a manufactured part is passed in the longitudinal direction 22 along the surface 18 of the calibration standard. The probe is adjusted in a conventional manner to normalize the response and set the system gain.

The previously described calibration standard 10 allows for quick eddy current probe calibration and reduces variation in the calibration. Further, because eddy current inspection results are used to determine the length of service remaining in the inspected part, reduction in calibration variation improves part life predictions, increases acceptable service intervals and reduces maintenance cost.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A calibration standard for calibrating an eddy current inspection probe sized and shaped to inspect a preselected non-planar feature of a manufactured part, said feature extending in a longitudinal direction and in a lateral direction and having an end profile as viewed in the longitudinal direction having a substantially invariant shape and orientation, said calibration standard comprising a body having a non-planar surface extending in a longitudinal direction and in a lateral direction and having an end profile as viewed in the longitudinal direction of the surface substantially identical to said profile of the feature, the surface of the body having an elongate narrow opening extending into the body substantially normal to the surface and traversing the surface of the body at a substantially constant angle with respect to the longitudinal direction of the surface as viewed normal to the surface.

2. A calibration standard as set forth in claim 1 wherein the constant angle is between about 45 degrees and about 55 degrees.

3. A calibration standard as set forth in claim 2 wherein the constant angle is about 50 degrees.

4. A calibration standard as set forth in claim 1 wherein the opening extends entirely through the body.

5. A calibration standard as set forth in claim 4 wherein the body is formed in two pieces having mating faces, the opening being defined by said mating faces.

* * * * *